United States Patent
Lassalle et al.

(10) Patent No.: US 6,252,082 B1
(45) Date of Patent: Jun. 26, 2001

(54) PYRIDONE DERIVATIVES, THEIR PREPARATION AND THEIR USE AS SYNTHESIS INTERMEDIATES

(75) Inventors: Gilbert Lassalle, Les Molières; Patrice Bellevergue, Paris; Jean-Claude Bourbier, Bretigny sur Orge; Daniel Galtier, Guyancourt; Valérie Martin, Villejuif, all of (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/341,574

(22) PCT Filed: Jan. 13, 1998

(86) PCT No.: PCT/FR98/00044

§ 371 Date: Jul. 14, 1999

§ 102(e) Date: Jul. 14, 1999

(87) PCT Pub. No.: WO98/31671

PCT Pub. Date: Jul. 23, 1998

(30) Foreign Application Priority Data

Jan. 16, 1997 (FR) .................................................... 9700378

(51) Int. Cl.[7] .................................................. C07D 211/86
(52) U.S. Cl. ..................... 546/293; 546/293; 546/294; 546/296; 546/297; 546/256; 546/280.4; 546/281.4; 546/13
(58) Field of Search .................................. 546/293, 294, 546/296, 297, 256, 280.4, 281.4, 13

(56) References Cited

FOREIGN PATENT DOCUMENTS 0 677 525   10/1995   (EP) .
0 718 307   6/1996    (EP) .

OTHER PUBLICATIONS

CA 127:234607 ,abstract for pat' 5,656,930 , Tamura et al., 1997.*

* cited by examiner

Primary Examiner—Jane Fan
(74) Attorney, Agent, or Firm—Finnegan, Henderson, Farabow, Garrett & Dunner, L.L.P.

(57) ABSTRACT

The invention concerns compounds of formula (I)

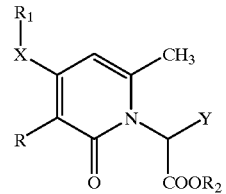

(I)

in which: R is $-NO_2$ or $-NHR_3$, $R_3$ being hydrogen, $-COR_4$ ($R_4$ selected among ($C_1-C_4$) alkyl, aryl and aryl ($C_1-C_4$) alkyl, $-COOR_5$ ($R_5$ selected among ($C_1-C_4$) alkyl and aryl ($C_1-C_4$) alkyl), $-CONHR_6$ or $SO_2R_6$ ($R_6$ selected among ($C_1-C_5$) alkyl, aryl and aryl($C_1-C_4$) alkyl), $-SO_2NR_7R_8$ ($R_7$ and $R_8$ independently of each other represent hydrogen or ($C_1-C_4$) alkyl or form with the nitrogen atom a morpholine group), aryl ($C_1-C_4$) alkyl, $R_1$ is a ($C_1-C_4$) alkyl group linear or branched, cyclo ($C_3-C_8$) alkyl, aryl optionally substituted, aryl ($C_1-C_4$) alkyl optionally substituted, heteroaryl, $R_2$ is a hydrogen atom, a ($C_1-C_4$) alkyl or arylmethyl group, X is an oxygen or sulphur atom, a $-CH_2-$, $-SO_2$ or $-NR_1-$ group and Y is a hydrogen atom or ($C_1-C_6$) alkyl. The invention is applicable to synthesis intermediates.

23 Claims, No Drawings

PYRIDONE DERIVATIVES, THEIR PREPARATION AND THEIR USE AS SYNTHESIS INTERMEDIATES

The Patent Application EP 677 525 relates to derivatives of aminoboronic acids of formula

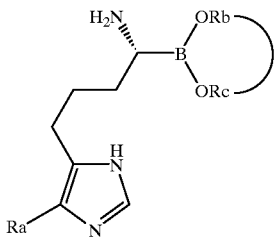

which are useful as synthesis intermediates.

The Patent Application EP 718 307 relates to 1-oxo-2-(phenylsulphonylamino)pentylpiperidine derivatives of formula

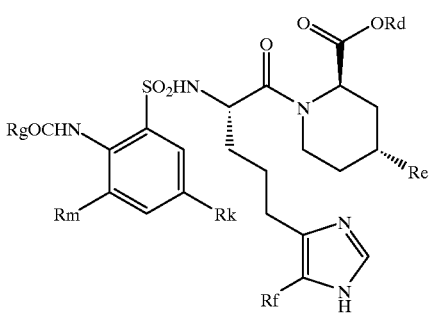

which are useful in thrombosis-related clinical indications.

The subject of the present invention is pyridone derivatives, their preparation and their use as synthesis intermediates.

The compounds according to the invention correspond to the formula (I)

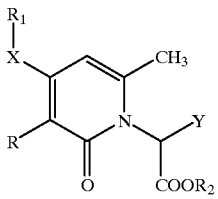

in which

R represents either an —$NO_2$ group, or an —$NHR_3$ group, $R_3$ being a hydrogen atom, a —$COR_4$ group (where $R_4$ is selected from the ($C_1$–$C_4$)alkyl, aryl and aryl($C_1$–$C_4$)alkyl groups), a —$COOR_5$ group (where $R_5$ is selected from the ($C_1$–$C_4$)alkyl and aryl($C_1$–$C_4$)alkyl groups), a —$CONHR_6$ group, an —$SO_2R_6$ group (where $R_6$ is selected from the ($C_1$–$C_5$)alkyl, aryl and aryl($C_1$–$C_4$)alkyl groups), an —$SO_2NR_7R_8$ group (where $R_7$ and $R_8$ are each, independently of each other, a hydrogen atom or a ($C_1$–$C_4$)alkyl group or form with the nitrogen atom carrying them a morpholine group), an aryl($C_1$–$C_4$)alkyl group (the aryl group being optionally substituted with a halogen atom, a linear or branched ($C_1$–$C_5$)alkyl group, a trifluoromethyl group, a cyano group, a ($C_1$–$C_4$)alkoxycarbonyl group or a ($C_1$–$C_4$)acylamino group), a heteroaryl ($C_1$–$C_4$)alkyl group, $R_1$ represents either a linear or branched ($C_1$–$C_4$)alkyl group, or a cyclo($C_1$–$C_8$)alkyl group, or an aryl group which is optionally substituted with a halogen atom, a linear or branched ($C_1$–$C_5$)alkyl group, a trifluoromethyl group, a cyano group, a ($C_1$–$C_4$)alkoxycarbonyl group or a ($C_1$–$C_4$)acylamino group, or an aryl($C_1$–$C_4$) alkyl group whose aryl group is optionally substituted as above, or a heteroaryl group, $R_2$ represents either a hydrogen atom, or a ($C_1$–$C_4$)alkyl group, or an arylmethyl group, X represents either an oxygen or sulphur atom, or a a linear or branched ($C_1$–$C_5$)alkyl group, a trifluoromethyl group, a cyano group, a ($C_1$–$C_4$)alkoxycarbonyl group or a ($C_1$–$C_4$)acylamino group), a heteroaryl ($C_1$–$C_4$)alkyl group, $R_1$ represents either a linear or branched ($C_1$–$C_4$)alkyl group, or a cyclo($C_3$–$C_8$)alkyl group, or an aryl group which is optionally substituted with a halogen atom, a linear or branched ($C_1$–$C_5$)alkyl group, a trifluoromethyl group, a cyano group, a ($C_1$–$C_4$)alkoxycarbonyl group or a ($C_1$–$C_4$)acylamino group, or an aryl($C_1$–$C_4$) alkyl group whose aryl group is optionally substituted as above, or a heteroaryl group, $R_2$ represents either a hydrogen atom, or a ($C_1$–$C_4$)alkyl group, or an arylmethyl group, X represents either an oxygen or sulphur atom, or a —$CH_2$—, —$SO_2$— or —$NR_1$— group where $R_1$ is as defined above, and Y represents either a hydrogen atom, or a linear or branched ($C_1$–$C_6$)alkyl group.

In the preceding definitions, the aryl groups are carbon-containing aromatic rings, for example phenyl, naphthyl or anthracenyl, and the heteroaryl groups are aromatic heterocycles such as for example pyridine or thiophene.

When Y is different from a hydrogen atom, then the compounds may exist in the form of pure enantiomers or racemates or a mixture of enantiomers which also form part of the invention.

The compounds of formula (Ia) to (Id) in which $R_1$ represents either a linear or branched ($C_1$–$C_4$)alkyl group, or a cyclo($C_3$–$C_8$)alkyl group, X an oxygen atom, $R_2$ a hydrogen atom or a ($C_1$–$C_4$)alkyl group and $R_3$ and Y are as defined above may be synthesized according to scheme 1.

The compound of formula (II) in which Y is as defined above and Alk represents a ($C_1$–$C_4$)alkyl group is reacted with a compound of formula $R_1OH$ under the Mitsunobu conditions, for example in the presence of triphenylphosphine ($PPh_3$) and of diethylazodicarboxylate (DEAD) and a compound of formula (Ia) is obtained which corresponds to a compound of formula (I) in which R is an —$NO_2$ group and X an oxygen atom.

In order to obtain a compound of formula (Ib) which corresponds to a compound of formula (I) in which R is an —$NH_2$ group and X an oxygen atom, the corresponding compound of formula (Ia) is subjected to a hydrogenation.

In order to obtain a compound of formula (Ic) which corresponds to a compound of formula (I) in which R is an —$NHR_3$ group, $R_3$ being as defined above and different from a hydrogen atom and X an oxygen atom, then the corresponding compound of formula (Ib) is treated either with a compound $R_3$-Hal where Hal represents a halogen atom, or with a compound of formula $R_6NCO$, or it is subjected to a reductive amination when $R_3$ represents an aryl($C_1$–$C_4$)alkyl group.

Scheme 1

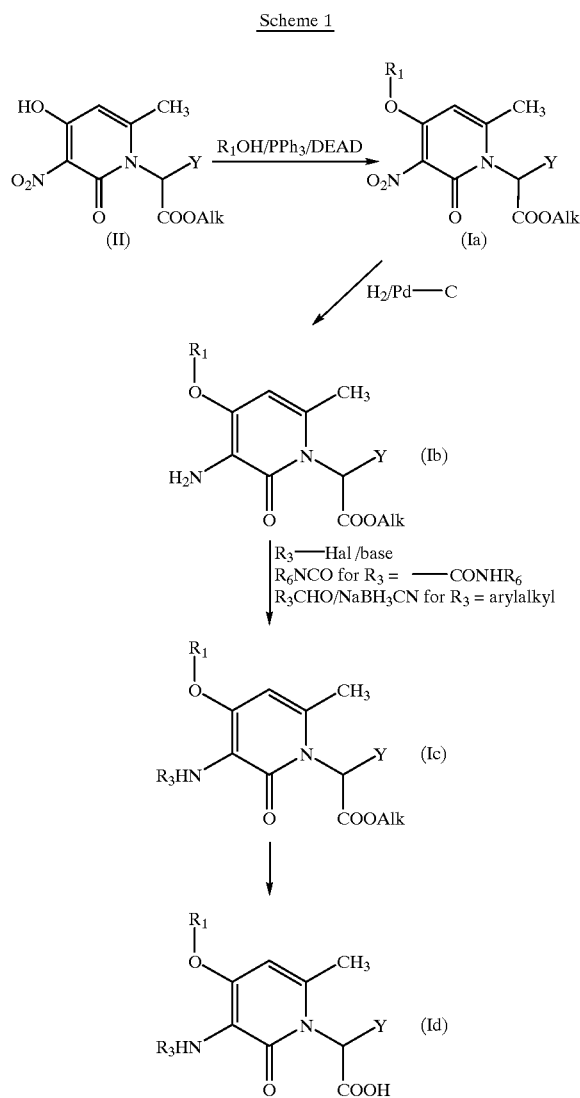

If it is desired to obtain a compound of formula (Id) which corresponds to a compound of formula (I) in which R is an —$NHR_3$ group, $R_3$ being as defined above and different from a hydrogen atom, $R_2$ a hydrogen atom and X an oxygen atom, then the corresponding compound of formula (Ic) is subjected to a saponification with sodium or lithium hydroxide.

To prepare the compounds of formula (Ie) to (Ii) in which $R_1$ represents either an aryl group optionally substituted with a halogen atom, a linear or branched ($C_1$–$C_5$)alkyl group, a trifluoromethyl group, a cyano group or a ($C_1$–$C_4$)acylamino group, or an aryl($C_1$–$C_4$)alkyl group optionally substituted as above, or a heteroaryl group, X represents either a sulphur atom or a —$CH_2$—, —$SO_2$— or —$NR_1$— group, $R_2$ represents a hydrogen atom or a ($C_1$–$C_4$)alkyl group and $R_3$ and Y are as defined above or in which $R_1$ represents either a linear or branched ($C_1$–$C_4$)alkyl group, or a cyclo($C_3$–$C_8$) alkyl group, X a sulphur atom or an —$NR_1$— group, $R_2$ represents a hydrogen atom or a ($C_1$–$C_4$)alkyl group and $R_3$ and Y are as defined above or in which $R_1$ represents either an aryl group optionally substituted with a halogen atom, a linear or branched ($C_1$–$C_5$)alkyl group, a trifluoromethyl group, a cyano group or a ($C_1$–$C_4$)acylamino group, or a heteroaryl group, X represents an oxygen atom, $R_2$ represents a hydrogen atom or a ($C_1$–$C_4$)alkyl group and $R_3$ and Y are as defined above, it is possible to use the process illustrated by scheme 2.

The alcohol function of the compound of formula (II) is converted under conventional conditions in order to obtain a compound of formula (III) in which OP represents a leaving group and then this compound is reacted either with a compound of formula $R_1XH$ where X is different from —$CH_2$—, or with an organometallic of formula $R_1CH_2Cu(CN)ZnHal$ where Hal represents a halogen atom (for X=—$CH_2$—) and a compound of formula (Ie) is obtained which corresponds to a compound of formula (I) in which R represents an —$NO_2$ group.

Scheme 2

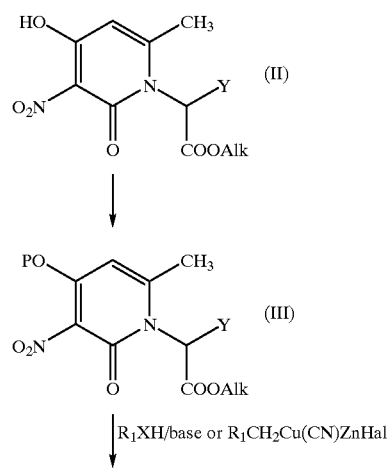

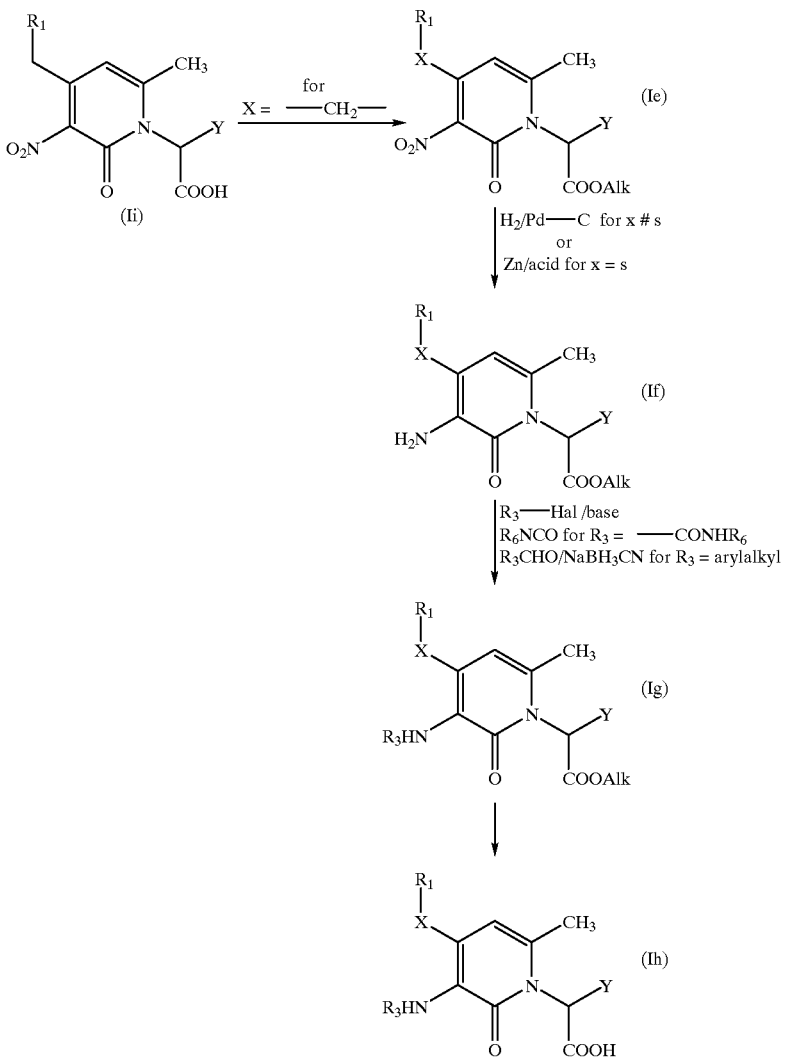

When it is desired to obtain a compound of formula (If) which corresponds to a compound of formula (I) in which R represents an —$NH_2$ group, then the corresponding compound of formula (Ie) is subjected to a hydrogenation, when X represents an oxygen atom or a —$CH_2$—, —$SO_2$—or —$NR_1$— group, or to a treatment with zinc in acidic medium when X represents a sulphur atom.

In order to obtain a compound of formula (Ig) which corresponds to a compound of formula (I) in which R represents an —$NHR_3$ group where $R_3$ is as defined above and is different from a hydrogen atom, then the corresponding compound of formula (If) is treated either with a compound $R_3$-Hal where Hal represents a halogen atom, or with a compound of formula $R_6NCO$, or it is subjected to a reductive amination when $R_3$ represents an aryl($C_1$–$C_4$)alkyl group.

If it is desired to obtain a compound of formula (Ih) in which $R_2$ represents a hydrogen atom, then the corresponding compound of formula (Ig) is subjected to a saponfication with sodium or lithium hydroxide.

If it is desired to obtain a compound of formula (Ii) in which R represents an —$NO_2$ group, X represents a —$CH_2$— group and $R_2$ a hydrogen atom, then the corresponding compound of formula (Ie) is subjected to a saponification with sodium or lithium hydroxide.

To prepare the compounds of formula (Ij) and (Ik) in which $R_1$ represents an aryl group or an aryl($C_1$–$C_4$)alkyl group which are substituted with a ($C_1$–$C_4$)alkoxycarbonyl group, the process illustrated by scheme 3 is used. A compound of formula (IV) in which Y is as defined above is reacted with a compound of formula ArOH in which Ar represents an arylmethyl group, in the presence of 1,3-dicyclohexylcarbodiimide and a compound of formula (V) is obtained whose alcohol function is converted under conventional conditions and a compound of formula (VI) is obtained in which OP represents a leaving group, which compound is reacted with a compound of formula $R_1XH$ where X is different from —$CH_2$— or with a compound of formula $R_1CH_2Cu(CN)ZnHal$ (for X=—$CH_2$—) and a compound of formula (Ij) is obtained which corresponds to a compound of formula (I) in which R represents an —$NO_2$ group and $R_2$ an arylmethyl group.

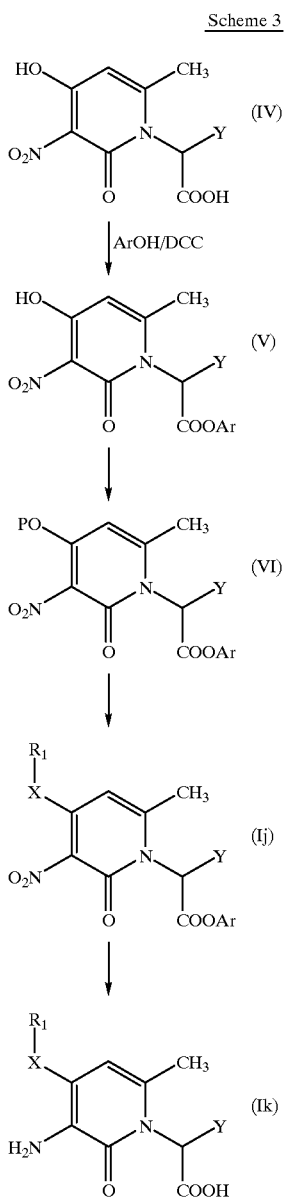

Scheme 3

In order to obtain a compound of formula (Ik) which corresponds to a compound of formula (I) in which R represents an —NH$_2$ group and R$_2$ a hydrogen atom, then the corresponding compound of formula (Ij) is subjected to a catalytic hydrogenation.

The compounds of formula (I) in which X represents an —SO$_2$— group may also be prepared from the corresponding compound of formula (I) in which X represents a sulphur atom by treating with 3-chloro-peroxybenzoic acid.

The starting compounds are commercially available or are described in the literature or may be prepared according to methods which are described therein or which are known to persons skilled in the art.

Thus, the preparation of 4-hydroxy-6-methyl-2-oxo-1,2-dihydropyridine-1-acetic acid is carried out from 4-hydroxy-6-methyl-2H-pyran-2-one according to the technique described by S. Garrat et al., (1963), J. Org. Chem., 1372. To prepare the compounds of formula (II), a nitration of the 4-hydroxy-6-methyl-2-oxo-1,2-dihydropyridine-1-acetic acid is carried out under conventional conditions known to persons skilled in the art and then the compound obtained is esterified in an acid medium. The organometallics of formula R$_1$CH$_2$Cu(CN)ZnHal are prepared according to the method described by P. Knochel et al., Chemical Reviews, (1993), 93, 2117.

The examples which follow illustrate the preparation of some compounds in accordance with the invention.

The elemental microanalyses and the IR and NMR spectra confirm the structure of the compounds obtained. The numbers for the compounds exemplified refer to those in the table given later.

EXAMPLE 1 (compound No. 6)

Methyl 6-Methyl-3-nitro-2-oxo-4-(phenylmethyl)-1,2-dihydropyridine-1-acetate 1.1. 4-Hydroxy-6-methyl-2-oxo-1,2-dihydropyridine-1-acetic Acid 178.7 g (1.4 mmol) of 4-hydroxy-6-methyl-2H-pyran-2-one are added, in portions at room temperature, to a solution of 106.4 g (1.4 mmol) of glycine in 1.4 l of a 1 N aqueous sodium hydroxide solution. The mixture is heated under reflux for 1 hour, the reaction medium is cooled and it is acidified with 500 ml of 3 N hydrochloric acid. The reaction medium is then concentrated to half the volume, the precipitate is filtered, it is washed with cold water and it is dried in an oven.

175 g of product are obtained in the form of a white solid.
Yield=70%; Melting point=240° C.

1.2. 4-Hydroxy-6-methyl-3-nitro-2-oxo-1,2-dihydropyridine-1-acetic Acid 31.2 g (0.17 mol) of 4-hydroxy-6-methyl-2-oxo-1,2-dihydropyridine-1-acetic acid are suspended in 255 ml of acetic acid, 24 ml of a 68% aqueous nitric acid solution are added at room temperature and the mixture is heated to 80° C. on an oil bath. The reaction medium is cooled, the solvent is evaporated off and the residue is taken up in twice 100 ml of water. The mixture is evaporated to dryness and the residue is taken up with twice 100 ml of toluene. The product is recrystallized from isopropanol and dried in an oven. 27.2 g of product are obtained in the form of yellow crystals.
Yield=70%; Melting point=205° C.

1.3. Methyl 4-hydroxy-6-methyl-3-nitro-2-oxo-1,2-dihydropyridine-1-acetate 250 ml of methanol are saturated with a gaseous hydrochloric acid stream and 25 g (0.11 mol) of 4-hydroxy-6-methyl-3-nitro-2-oxo-1,2-dihydropyridine-1-acetic acid are introduced in portions. The mixture is heated at reflux temperature for 4 hours and then the precipitate is filtered and it is dried in an oven. 23 g of product are obtained in the form of yellow crystals.
Yield=85%; Melting point=187° C.

1.4. Methyl 6-methyl-3-nitro-2-oxo-4-[[(trifluoromethyl)sulphonyl]oxy]-1,2-dihydropyridine-1-acetate 17.4 ml of triethylamine are added to 26.9 g (0.11 mol) of methyl 4-hydroxy-6-methyl-3-nitro-2-oxo-1,2-dihydropyridine-1-acetate in suspension in 500 ml of dichloromethane and the mixture is cooled to −70° C. 20 ml (0.12 mol) of trifluoromethanesulphonic anhydride are then added dropwise, the reaction medium is stirred for 1 hour at room temperature and then it is washed successively with 200 ml of water and 100 ml of an ice-cold 1 N hydrochloric acid solution. The organic phase is dried over magnesium sulphate and evaporated to dryness. The residue is purified by chromatography on a silica gel column, eluting with a dichloro-methane:methanol (98:2) mixture and then the product is precipitated from ether.

40.8 g of product are obtained in the form of yellow crystals.
Yield=98%; Melting point=68–70° C.

1.5. Methyl 6-methyl-3-nitro-2-oxo-4-(phenylmethyl)-1,2-dihydropyridine-1-acetate 200 μl of chlorotrimethylsilane are added at room temperature to 2 g (30.6 mmol) of zinc in suspension in 50 ml of tetrahydrofuran, the mixture is kept stirred for 0.5 hour at room temperature and then it is cooled to 0° C. 4.5 g (26.3 mmol) of phenylmethyl bromide in solution in 20 ml of tetrahydrofuran are then added dropwise and then the reaction medium is kept stirred for 2 hours at this temperature. Next, the mixture is transferred to a three-necked flask containing 2.24 g (25 mmol) of copper(I) cyanide and 2.12 g (50 mmol) of lithium chloride at −10° C., the mixture is stirred at this temperature for 5 minutes and then cooled to −70° C. 7.3 g (19.5 mmol) of methyl 6-methyl-3-nitro-2-oxo-4-[[(trifluoromethyl)sulphonyl]oxy]-1,2-dihydropyridine-1-acetate in solution in 50 ml of tetrahydrofuran are then added dropwise, the temperature of the reaction medium is allowed to return to 0° C. and the stirring is maintained for 1 hour at this temperature. The mixture is then poured over 100 ml of a 1 N hydrochloric acid solution and 200 ml of dichloromethane are added. The precipitate is filtered, the filtrate is allowed to settle out and the aqueous phase is extracted with dichloromethane. The organic phases are combined, they are dried over magnesium sulphate and evaporated to dryness. The residue is purified by chromatography on a silica gel column, eluting with a dichloromethane:methanol (98:2) mixture.

5.3 g of product are obtained in the form of yellow crystals which are recrystallized from ethanol
Yield=86%; Melting point=146–147° C.

EXAMPLE 2 (compound No. 20)

Methyl 3-Amino-6-methyl-2-oxo-4-(phenylmethyl)-1,2-dihydropyridine-1-acetate 10 g (31.6 mmol) of methyl 6-methyl-3-nitro-2-oxo-4-(phenylmethyl)-1,2-dihydropyridine-1-acetate are placed in a Parr flask and 150 ml of methanol are added. 1 g of 10% palladium on carbon is then introduced and the mixture is hydrogenated at 0.28 MPa (40 psi) at room temperature for 2 hours. The mixture is filtered on celite and the solvent is evaporated to dryness.

9 g of product are obtained which are recrystallized from ethanol in the form of a white solid.
Yield=99%; Melting point=135° C.

EXAMPLE 3 (compound No. 41)

6-Methyl-2-oxo-3-[[(phenylmethoxy)carbonyl]amino]-4-(phenylmethyl)-1,2-dihydropyridine-1-acetic Acid 1.17 g (11 mmol) of sodium carbonate and then, dropwise, 1.4 ml (8.4 mmol) of phenylmethyl chloroformate are added to a solution of 2.11 g (7.4 mmol) of methyl 3-amino-6-methyl-2-oxo-4-(phenylmethyl)-1,2-dihydropyridine-1-acetate in solution in 50 ml of tetrahydrofuran and the mixture is kept stirred overnight at room temperature. The mixture is evaporated, the residue is taken up in 50 ml of dichloromethane and washed successively with 20 ml of water and 20 ml of a saturated aqueous sodium chloride solution. It is dried under vacuum and evaporated to dryness.

3 g of product are obtained which are used as such in the next stage.
Yield=97%.

The product obtained is dissolved in 20 ml of a water:tetrahydrofuran (1:1) mixture, 320 mg (7.62 mmol) of lithium hydroxide monohydrate are added and the mixture is kept stirred for 3 hours at room temperature. The solvent is evaporated, the aqueous phase is acidified to pH=1 with a 1 N aqueous hydrochloric acid solution and the mixture is extracted with twice 50 ml of dichloromethane. It is washed with 20 ml of a saturated sodium chloride solution, dried over magnesium sulphate and evaporated to dryness. 2.25 g of product are obtained in the form of a white powder which is recrystallized from isopropanol.

Yield=75%; Melting point=158–160° C.

EXAMPLE 4 (compound No. 51)

6-Methyl-2-oxo-4-(phenylmethyl)-3-[[(phenylmethyl)sulphonyl]amino]-1,2-dihydropyridine-1acetic Acid 1 ml (7.17 mmol) of triethylamine and 0.95 g (5 mmol) of (phenylmethyl)sulphonyl chloride are added to 1 g (3.5 mmol) of methyl 3-amino-6-methyl-2-oxo-4-(phenylmethyl)-1,2-dihydropyridine-1-acetate in solution in 30 ml of dichloromethane and the mixture is kept stirred for 12 hours at room temperature. The reaction medium is washed successively with 10 ml of water, 10 ml of a 1 N aqueous hydrochloric acid solution and then 10 ml of a saturated sodium chloride solution. The medium is dried over magnesium sulphate and evaporated. The residue is purified by chromatography on a silica gel column, eluting with a dichloromethane:methanol (98:2) mixture. The product is used as such in the hydrolysis stage which is carried out according to the procedure described in Example 3. 0.8 g of product is obtained in the form of a white powder.

Yield=54%; Melting point>200° C.

EXAMPLE 5 (compound No. 52)

6-Methyl-3-[(morpholin-4-ylsulphonyl)amino]-2-oxo-4-(phenylmethyl)-1,2-dihydropyridine-1-acetic Acid 1 ml (6.8 mmol) of morpholin-4-ylsulphonyl chloride and 1.1 ml (7.35 mmol) of 1,8-diazabicyclo[5.4.0]undec-7-ene are added every three days for 15 days to 1.75 g (6.1 mmol) of methyl 3-amino-6-methyl-2-oxo-4-(phenylmethyl)-1,2-dihydropyridine-1-acetate in solution in 10 ml of dichloromethane. 100 ml of dichloromethane are then added to the reaction medium and the medium is washed successively with 20 ml of water, 100 ml of an aqueous hydrochloric acid solution and 20 ml of a saturated sodium chloride solution, dried over magnesium sulphate and evaporated. The residue is purified by chromatography on a silica gel column, eluting with a dichloromethane:methanol (98:2) mixture and the product is recrystallized from ethanol. 1.4 g of product are obtained in the form of a white powder.

Yield=52%; Melting point=160–162° C.

The product obtained is hydrolysed according to the procedure of Example 3 using 4.8 ml of a 1 N aqueous sodium hydroxide solution.

1.1 g of product are obtained.
Melting point=158° C. (melting with decomposition).

EXAMPLE 6 (compound No. 47)

6-Methyl-2-oxo-4-(phenylmethyl)-3-[[[(phenylmethyl)amino]carbonyl]amino]-1,2-dihydropyridine-1-acetic Acid 1.56 ml (12.6 mmol) of benzylisocyanate and 0.1 g (1.05 mmol) of copper(I) chloride are added at 20° C. to 3 g (10.5 mmol) of methyl 3-amino-6-methyl-2-oxo-4-(phenylmethyl)-1,2-dihydropyridine-1-acetate in 20 ml of dimethylformamide. The mixture is kept stirred for 24 hours at room temperature, two times 75 ml of ethyl acetate are added and the mixture is washed successively with 20 ml of water and 20 ml of a saturated sodium chloride solution. The mixture is dried over sodium sulphate and evaporated to dryness. The residue is purified by chromatography on a silica gel column, eluting with a dichloromethane:methanol (98:2) mixture.

2.45 g of ester are obtained which are used as such.

Yield=56%.

The ester is dissolved in 20 ml of tetrahydrofuran. 6 ml of a 1 N sodium hydroxide solution are added, the mixture is left for 3 hours at 20° C. and then the reaction medium is acidified to pH=1 with a 1 N hydrochloric acid solution. The precipitate obtained is filtered, it is washed with water and it is dried. 2.27 g of product are obtained.

Yield=96%; Melting point=176° C.

EXAMPLE 7 (compound No. 53)

6-Methyl-2-oxo-4-(phenylmethyl)-3-[(pyridin-2-ylmethyl)amino]-1,2-dihydropyridine-1-acetic Acid 0.21 ml (1.75 mmol) of pyridine-2-carboxaldehyde is added to 0.5 g (1.75 mmol) of methyl 3-amino-6-methyl-2-oxo-4-(phenylmethyl)-1,2-dihydropyridine-1-acetate in solution in 20 ml of benzene and the mixture is heated at the reflux temperature for 3 hours. The solvent is evaporated off, 20 ml of methanol and then 154 mg (2.45 mmol) of sodium cyanoborohydride are added and the pH of the medium is adjusted to 5 with acetic acid. The reaction medium is left for 1.5 hours, the excess hydride is removed by addition of concentrated hydrochloric acid and the medium is evaporated to dryness. The residue is taken up with 10 ml of water and it is extracted with 20 ml of ether. The aqueous phase is recovered, the pH is adjusted to 5 with a sodium hydroxide solution, it is saturated with sodium chloride and it is extracted with five times 20 ml of ether. The medium is dried over magnesium sulphate, concentrated to dryness and the residue is purified by chromatography on a silica gel column, eluting with a dichloromethane:methanol (99:1) mixture.

0.44 g of ester is obtained which is directly hydrolysed.

Yield=67%.

0.44 g (1.16 mmol) of ester is placed in a water:methanol (1:1) mixture, 200 mg (4.76 mmol) of lithium hydroxide monohydrate are added and the mixture is stirred for 1 hour at room temperature. The solvent is evaporated and the pH of the aqueous phase is adjusted to 5 with acetic acid. The aqueous phase is extracted with three times 20 ml of dichloromethane, the medium is dried over magnesium sulphate and evaporated to dryness. The residue is taken up in twice 20 ml of benzene and evaporated. 400 mg of product are obtained in the form of a yellow foam.

Yield=85%; Melting point=63° C. (melting with decomposition).

EXAMPLE 8 (compound No. 15)

Methyl 6-methyl-3-nitro-2-oxo-4-(thien-3-ylmethyl)-1,2-dihydropyridine-1-acetate This compound is prepared from 5 g (13.4 mmol) of methyl 6-methyl-3-nitro-2-oxo-4-[[(trifluoromethyl)sulphonyl]oxy]-1,2-dihydropyridine-1-acetate and 2.9 g (16.4 mmol) of 3-bromomethyl-thiophene according to the method described in 1.5. 3.5 g of product are obtained in the form of yellow crystals.

Yield=84%; Melting point=157–158° C.

EXAMPLE 9 (compound No. 37)

Methyl 6-methyl-2-oxo-3-[[(phenylmethoxy)carbonyl]-amino]-4-(thien-3-ylmethyl)-1,2-dihydropyridine-1-acetate 9.1. Methyl 3-amino-6-methyl-2-oxo-4-(thien-3-ylmethyl)-1,2-dihydropyridine-1-acetate The methyl 6-methyl-3-nitro-2-oxo-4-(thien-3-ylmethyl)-1,2-dihydropyridine-1-acetate is hydrogenated under the conditions of 2. 3.2 g of product are obtained.

Yield=100%.

9.2. Methyl 6-methyl-2-oxo-3-[[(phenylmethoxy)-carbonyl]amino]-4-(thien-3-ylmethyl)-1,2-dihydropyridine-1-acetate This compound is prepared from 3.2 g (11 mmol) of methyl 3-amino-6-methyl-2-oxo-4-(thien-3-ylmethyl)-1,2-dihydropyridine-1-acetate according to the method described in Example 3. 3 g of product are obtained which are recrystallized from ethanol.

Yield=64%; Melting point=127–128° C.

EXAMPLE 10 (compound No. 44)

6-Methyl-2-oxo-3-[[(phenylmethoxy)carbonyl]amino]-4-(thien-3-ylmethyl)-1,2-dihydropyridine-1-acetic Acid 3 g (7 mmol) of methyl 6-methyl-2-oxo-3-[[(phenylmethoxy)carbonyl]amino]-4-(thien-3-ylmethyl)-1,2-dihydropyridine-1-acetate are hydrolysed according to the method described in Example 3. 2.2 g of product are obtained after recrystallization.

Yield=76%; Melting point=153–155° C.

EXAMPLE 11 (compound No. 9)

Methyl 4-[[4-(1,1-dimethylethyl)phenyl]methyl]-6-methyl-3-nitro-1,2-dihydropyridine-1-acetate This compound is prepared from 5 g (13.4 mmol) of methyl 6-methyl-3-nitro-2-oxo-4-[[(trifluoromethyl)sulphonyl]oxy]-1,2-dihydropyridine-1-acetate and 4.54 g (20 mmol) of 4-(1,1-dimethylethyl)phenylmethyl bromide according to the method described in 1.5. 3.5 g of product are obtained in the form of yellow crystals.

Yield=70%; Melting point=135° C.

EXAMPLE 12 (compound No. 42)

4-[[4-(1,1-Dimethylethyl)phenyl]methyl]-6-methyl-2-oxo-3-[[(phenylmethoxy)carbonyl]amino]-1,2-dihydropyridine-1-acetic Acid 12.1. Methyl 3-amino-4-[[4-(1,1-dimethylethyl)-phenyl]methyl]-6-methyl-2-oxo-1,2-dihydropyridine-1-acetate 2.05 g (5.51 mmol) of methyl 4-[[4-(1,1-dimethylethyl)phenyl]methyl]-6-methyl-3-nitro-2-oxo-1,2-dihydropyridine-1-acetate are hydrogenated under the conditions of Example 2. 1.9 g of product are obtained which are used as such in the next stage.

Yield=100%.

12.2. Methyl 4-[[4-(1,1-dimethylethyl)phenyl]-methyl]-6-methyl-2-oxo-3-[[(phenylmethoxy)-carbonyl]amino]-1,2-dihydropyridine-1-acetate This product is obtained from methyl 3-amino-4-[[4-(1,1-dimethylethyl)phenyl]methyl]-6-methyl-2-oxo-1,2- dihydropyridine-1-acetate according to the method described in Example 3.

2.28 g of product are obtained which are used as such in the next stage.

Yield=87%;

12.3. 4-[[4-(1,1-Dimethylethyl)phenyl]methyl]-6-methyl-2-oxo-3-[[(phenylmethoxy)carbonyl]-[amino]-1,2-dihydropyridine-1-acetic Acid 2.28 g of methyl 4-[[4-(1,1-dimethylethyl)-phenyl]methyl]-6-methyl-2-oxo-3-[[(phenylmethoxy)-carbonyl]amino]-1,2-dihydropyridine-1-acetate are hydrolysed under the conditions of Example 3. 1.8 g of product are obtained in the form of a white powder.

Yield=80%; Melting point=200° C.

EXAMPLE 13 (compound No. 8)

Methyl 4-[(4-fluorophenyl)methyl]-6-methyl-3-nitro-2-oxo-1,2-dihydropyridine-1-acetate This compound is prepared from 11 g (29.4 mmol) of methyl 6-methyl-3-nitro-2-oxo-4-[[(trifluoromethyl)sulphonyl]oxy]-1,2-dihydropyridine-1-acetate and 10 g (52.9 mmol) of (4-fluorophenyl)-methyl bromide according to the method described in 1.5.

6.85 g of product are obtained in the form of yellow crystals.

Yield=70%; Melting point=150° C.

EXAMPLE 14 (compound No. 21)

Methyl 3-amino-4-[(4-fluorophenyl)methyl]-6-methyl-2-oxo-1,2-dihydropyridine-1-acetate 4 g (12 mmol) of 4-[(4-fluorophenyl)methyl]-6-methyl-3-nitro-2-oxo-1,2-dihydropyridine-1-acetate are hydrogenated under the conditions of Example 2. 3.11 g of product are obtained after purification by chromatography on a silica gel column, eluting with a dichloromethane:methanol (98:2) mixture.

Yield=65%; Melting point=151 C.

EXAMPLE 15 (compound No. 36)

Methyl 4-[(4-fluorophenyl)methyl]-6-methyl-2-oxo-3-[[(phenylmethoxy)carbonyl]amino]-1,2-dihydropyridine-1-acetate 1.8 g (5.91 mmol) of methyl 3-amino-4-[(4-fluorophenyl)methyl]-6-methyl-2-oxo-1,2-dihydro-pyridine-1-acetate are treated with 1 ml (7.09 mmol) of phenylmethyl chloroformate according to the method described in Example 3. The residue is purified by chromatography on a silica gel column, eluting with a dichloromethane:methanol (98:2) mixture. 2.15 g of product are obtained.

Yield=83%; Melting point=236° C.

EXAMPLE 16 (compound No. 10)

Methyl 6-methyl-3-nitro-2-oxo-4-[[4-(trifluoromethyl)phenyl]methyl]-1,2-dihydropyridine-1-acetate This compound is prepared from 5.58 g (14.9 mmol) of methyl 6-methyl-3-nitro-2-oxo-4-[[(trifluoromethyl)sulphonyl]oxy]-1,2-dihydropyridine-1-acetate and 5 g (20.9 mmol) of [4-(trifluoromethyl)-phenyl]methyl bromide according to the method described in Example 1.5.

5.55 g of product are obtained in the form of yellow crystals.

Yield=97%; Melting point=155° C.

EXAMPLE 17 (compound No. 16)

6-Methyl-3-nitro-2-oxo-4-[[4-(trifluoromethyl)phenyl]-methyl-1,2-dihydropyridine-1-acetic Acid 1.67 g (4.35 mmol) of methyl 6-methyl-3-nitro-2-oxo-4-[[4-(trifluoromethyl)phenyl]methyl]-1,2-dihydropyridine-1-acetate are suspended in 5 ml of ethanol. 5.2 ml of a 1 N aqueous sodium hydroxide solution are added and the mixture is left for 4 hours at room temperature. The reaction medium is acidified with 5.5 ml of a 1 N aqueous hydrochloric acid solution, the precipitate is filtered, it is washed and it is dried.

1.52 g of product are obtained.

Yield=94%; Melting point=224° C.

EXAMPLE 18 (compound No. 11)

Methyl 4-[(4-cyanophenyl)methyl]-6-methyl-3-nitro-2-oxo-1,2-dihydropyridine-1-acetate This compound is prepared from 15.3 g (40.9 mmol) of methyl 6-methyl-3-nitro-2-oxo-4-[[(trifluoromethyl)sulphonyl]oxy]-1,2-dihydropyridine-1-acetate and 10 g (51 mmol) of (4-cyanophenyl)methyl bromide according to the method described in Example 1.5.

9.41 g of product are obtained in the form of yellow crystals.

Yield=68%; Melting point=195–196° C.

EXAMPLE 19 (compound No. 33)

4-[(4-cyanophenyl)methyl]-3-[(methoxycarbonyl)amino]-6-methyl-2-oxo-1,2-dihydropyridine-1-acetic Acid 19.1. Methyl 3-amino-4-[(4-cyanophenyl)methyl]-6-methyl-2-oxo-1,2-dihydropyridine-1-acetate 2 g (5.86 mmol) of methyl 4-[(4-cyanophenyl)-methyl]-6-methyl-3-nitro-2-oxo-1,2-dihydropyridine-1-acetate are hydrogenated under the conditions of Example 2.

1.75 g of product are obtained which are used as such in the next stage.

Yield=96%.

19.2. 4-[(4-Cyanophenyl)methyl]-3-[(methoxycarbonyl)amino]- 6-methyl-2-oxo-1,2-dihydropyridine-1-acetic Acid 1.4 g (4.5 mmol) of methyl 3-amino-4-[(4-cyanophenyl)methyl]-6-methyl-2-oxo-1,2-dihydropyidine-1-acetate are treated with 0.7 ml (5 mmol) of methyl chloroformate and then the compound obtained is hydrolysed according to the method described in Example 3.

1.7 g of product are obtained in the form of a white powder.

Yield=88%; Melting point=125–130° C.

EXAMPLE 20 (compound No. 3)

Methyl 4-(cyclohexylmethyl)-6-methyl-3-nitro-2-oxo-1,2-dihydropyridine-1-acetate This compound is prepared from 3 g (8 mmol) of methyl 6-methyl-3-nitro-2-oxo-4-[[(trifluoromethyl)-sulphonyl]oxy]-1,2-dihydropyridine-1-acetate and 5.45 g (24.3 mmol) of cyclohexylmethyl iodide according to the method described in Example 1.5. 1.3 g of product are obtained in the form of yellow crystals.

Yield=50%; Melting point=128° C.

EXAMPLE 21 (compound No. 38)

4-(Cyclohexylmethyl)-6-methyl-2-oxo-3-[[(phenylmethoxy)carbonyl]amino]-1,2-dihydropyridine-1-acetic Acid 21.1. Methyl 3-amino-4-(cyclohexylmethyl)-6-methyl-2-oxo-1,2-dihydropyridine-1-acetate 1.3 g (4 mmol) of methyl 4-(cyclohexylmethyl)-6-methyl-3-nitro-2-oxo-1,2-dihydropyridine-1-acetate are hydrogenated under the conditions of Example 2.

1.12 g of product are obtained which are used as such in the next stage.

Yield=95%.

21.2. Methyl 4-(cyclohexylmethyl)-6-methyl-2-oxo-3-[[(phenylmethoxy)carbonyl]amino]-1,2-dihydropyridine-1-acetate 1.12 g (3.83 mmol of methyl 3-amino-4-(cyclohexylmethyl)-6-methyl-2-oxo-1,2-dihydropyridine-1-acetate are reacted with phenylmethyl chloroformate under the conditions described in Example 3. 0.93 g of product is obtained after purification by chromatography on a silica gel column, eluting with a dichloromethane:methanol (98:2) mixture.

Yield=57%.

21.3. 4-(Cyclohexylmethyl)-6-methyl-2-oxo-3-[[(phenylmethoxy)carbonyl]amino]-1,2-dihydropyridine-1-acetic Acid 0.92 g (2.16 mmol) of methyl 4-(cyclohexylmethyl)-6-methyl-2-oxo-3-[[(phenylmethoxy)carbonyl]-amino]-1,2-dihydropyridine-1-acetate is hydrolysed under the conditions described in Example 3. 0.8 g of product is obtained.

Yield=90%; Melting point=150° C.

EXAMPLE 22 (compound No. 24)

3-Amino-4-[[4-(methoxycarbonyl)phenyl]methyl]-6-methyl-2-oxo-1,2-dihydropyridine-1-acetic Acid 22.1. Phenylmethyl 4-hydroxy-6-methyl-3-nitro-2-oxo-1,2-dihydropyridine-1-acetate 0.5 g (2.19 mmol) of 4-hydroxy-6-methyl-3-nitro-2-oxo-1,2-dihydropyridine-1-acetic acid is suspended in 5 ml of dichloromethane, 250 μgl (2.41 mmol) of benzyl alcohol and 0.5 g (2.45 mmol) of 1,3-dicyclohexylcarbodiimide in solution in 5 ml of dichloromethane are added. The mixture is kept stirred for 3 hours at room temperature, it is diluted with 20 ml of dichloromethane, filtered and evaporated. The residue is recrystallized from ethanol. 0.57 g of product is obtained.

Yield=82%; Melting point=146–147° C.

22.2. Phenylmethyl 6-methyl-3-nitro-2-oxo-4-[[(trifluoromethyl)sulphonyl]oxy]-1,2-dihydropyridine-1-acetate It is prepared from 8 g (25.2 mmol) of phenylmethyl 4-hydroxy-6-methyl-3-nitro-2-oxo-1,2-dihydropyridine-1-acetate and trifluoromethanesulphonic anhydride according to the method described in Example 1.4.

9.5 g of product are obtained in the form of a beige solid.

Yield=83%; Melting point=115–118° C.

22.3. Phenylmethyl 4-[[4-(methoxycarbonyl)phenylmethyl]-6-methyl-3-nitro-2-oxo-1,2-dihydropyridine-1-acetate It is prepared from 6.6 g (14.6 mmol) of phenylmethyl 6-methyl-3-nitro-2-oxo-4-[[(trifluoromethyl) sulphonyl] oxy]-1,2-dihydropyridine-1-acetate and 4.58 g (20 mmol) of (4-methoxycarbonyl)phenylmethyl bromide according to the method described in Example 1.5, the intermediate zinc compound being added at −30° C.

4.5 g of product are obtained in the form of a yellow powder which is used as such in the next stage.

Yield=68%.

22.4. 3-amino-4-[[4-(methoxycarbonyl)phenyl]-methyl]-6-methyl-2-oxo-1,2-dihydropyridine-1-acetic Acid 3.7 g (8.2 mmol) of phenylmethyl 4-[[4-(methoxycarbonyl)phenyl]methyl -6-methyl-3-nitro-2-oxo-1,2-dihydropyridine-1-acetate are hydrogenated under the conditions described in Example 2.

2.2 5 g of product are obtained which are recrystallized from ethanol.

Yield=83%; Melting point=178–180° C.

EXAMPLE 23 (compound No. 12)

Methyl 4-[[4-(acetylamino)phenyl]methyl]-6-methyl-3-nitro-2-oxo-1,2-dihydropyridine-1-acetate It is prepared from 7.3 g (27 mmol) of N-acetyl-N-[4-(bromomethyl)phenyl]acetamide and 4 g (13.4 mmol) of methyl 6-methyl-3-nitro-2-oxo-4-[[(trifluoromethyl)sulphonyl]oxy]-1,2-dihydropyridine-1-acetate. The crude product is treated with ammonia.

2.1 g of product are obtained in the form of yellow crystals.

Yield=53%; Melting point=215° C.

EXAMPLE 24 (compound No. 4)

Methyl 6-methyl-3-nitro-2-oxo-4-phenoxy-1,2-dihydropyridine-1-acetate 1.38 g (14.7 mmol) of phenol in solution in 20 ml of tetrahydrofuran are added dropwise to a suspension of 0.58 g (14.5 mmol) of sodium hydride in tetrahydrofuran. The mixture is left for 0.5 hour at room temperature, it is cooled to −70° C. and 5.24 g (14 mmol) of methyl 6-methyl-3-nitro-2-oxo-4-[[(tri fluoromethyl)sulphonyl]oxy]-1,2-dihydropyridine-1-acetate in solution in 20 ml of tetrahydrofuran are added dropwise. The temperature of the reaction medium is allowed to return to 0° C. and the medium is stirred at this temperature for 1 hour. The mixture is poured over 20 ml of a 1 N aqueous hydrochloric acid solution and extracted with twice 200 ml of dichloromethane. The medium is washed with 100 ml of a saturated sodium chloride solution, dried over magnesium sulphate and evaporated. The product is recrystallized from methanol.

3.8 g of product are obtained in the form of yellow crystals.

Yield=85%; Melting point=239° C.

EXAMPLE 25 (compound No. 18)

Methyl 3-amino-6-methyl-2-oxo-4-phenoxy-1,2-dihydropyridine-1-acetate 3.3 g (10.4 mmol) of methyl 6-methyl-3-nitro-2-oxo-4-phenoxy-1,2-dihydropyridine-1-acetate are hydrogenated according to the method described in Example 2.

2.9 g of product are obtained which are recrystallized from ethanol in the form of a white solid.

Yield=96%; Melting point=105–106° C.

EXAMPLE 26 (compound No. 39)

6-Methyl-2-oxo-4-phenoxy-3-[[(phenylmethoxy)carbonyl]-amino]-1,2-dihydropyridine-1-acetic Acid 26.1. Methyl 6-methyl-2-oxo-4-phenoxy-3-[[(phenylmethoxy)carbonyl]amino]-1,2-dihydropyridine-1-acetate 2.5 g (7.9 mmol) of methyl 3-amino-6-methyl-2-oxo-4-phenoxy-1,2-dihydropyridine-1-acetate are treated with 1.7 ml (11.9 mmol) of phenylmethyl chloroformate under the conditions of Example 3.

3.2 g of product are obtained which are used as such in the next stage.

26.2. 6-Methyl-2-oxo-4-phenoxy-3-[[(phenylmethoxy)carbonyl]amino]-1,2-dihydropyridine-1-acetic Acid 3.2 g (7.6 mmol) of methyl 6-methyl-2-oxo-4-phenoxy-3-[[(phenylmethoxy)carbonyl]amino]-1,2-dihydropyridine-

EXAMPLE 27 (compound No. 1)

Methyl 6-methyl-4-(1-methylethoxy)-3-nitro-2-oxo-1,2-dihydropyridine-1-acetate

A solution of 11.38 g (43.4 mmol) of triphenylphosphine in 80 ml of benzene is cooled to 0° C. and 10 g (41.3 mmol) of methyl 4-hydroxy-6-methyl-3-nitro-2-oxo-1,2-dihydropyridine-1-acetate and 3.30 ml (43.37 mmol) of isopropanol are added. 6.83 ml (43.4 mmol) of diethylazodicarboxylate are then added dropwise and the mixture is left stirred for 48 hours. The reaction medium is washed successively with 50 ml of a saturated sodium hydrogen carbonate solution, 50 ml of water and 50 ml of a saturated sodium chloride solution. The medium is dried over magnesium sulphate and evaporated to dryness. The residue is purified by chromatography on a silica gel column, eluting with a dichloromethane:methanol (98:2) mixture.
9.45 g of product are obtained which recrystallize from ethyl acetate.
Yield=88%; Melting point=158° C.

EXAMPLE 28 (compound No. 5)

Methyl 6-methyl-3-nitro-2-oxo-4-(phenylthio)-1,2-dihydropyridine-1-acetate 1.5 ml (14.6 mmol) of thiophenol are placed in 20 ml of tetrahydrofuran and 2.1 ml (15.1 mmol) of triethylamine are added. 5.24 g (14 mmol) of methyl 6-methyl-3-nitro-2-oxo-4- [[(trifluoromethyl)sulphonyl]-oxy]-1,2-dihydropyridine-1-acetate are added dropwise at room temperature, the mixture is left for 5 minutes at room temperature and then it is poured over 20 ml of a 1 N aqueous hydrochloric acid solution. The reaction medium is extracted with twice 20 ml of dichloromethane, washed with 20 ml of a saturated sodium chloride solution and dried over magnesium sulphate and evaporated to dryness. The residue is washed with ether and it is dried.
4.67 g of product are obtained in the form of a yellow solid.
Yield=100%; Melting point=195° C.

EXAMPLE 29 (compound No. 19)

Methyl 3-amino-6-methyl-2-oxo-4-(phenylthio)-1,2-dihydropyridine-1-acetate 4.67 g (14 mmol) of methyl 6-methyl-3-nitro-2-oxo-4-(phenylthio)-1,2-dihydropyridine-1-acetate are suspended in 200 ml of a methanol:water (1:1) mixture, 5 ml of a 2 N aqueous hydrochloric acid solution and 5 g (76.4 mmol) of zinc are added successively and the mixture is heated at the reflux temperature for 3 hours. The reaction medium is allowed to cool, filtered and the solvent is evaporated. The medium is neutralized with 200 ml of sodium hydrogen carbonate and extracted with twice 100 ml of dichloromethane. The organic phase is recovered and it is dried and evaporated. The residue is purified by chromatography on a silica gel column, eluting with a dichloromethane:methanol (98:2) mixture. 2 g of product are obtained in the form of a white solid which are recrystallized from ethanol.
Yield=47%; Melting point=65–66° C.

EXAMPLE 30 (compound No. 40)

6-Methyl-2-oxo-3-[[(phenylmethoxy)carbonyl]amino]-4-(phenylthio)-1,2-dihydropyridine-1-acetic Acid 30.1. Methyl 6-methyl-2-oxo-3-[[(phenylethoxy)-carbonyl]amino]-4-(phenylthio)-1,2-dihydropyridine-1-acetate 1.7 g (5.6 mmol) of methyl 3-amino-6-methyl-2-oxo-4-(phenylthio)-1,2-dihydropyridine-1-acetate are treated with 1.2 ml (8.4 mmol) of phenylmethyl chloroformate under the conditions described in Example 3.
2.45 g of product are obtained in the form of a brown foam after purification by chromatography on a silica gel column, eluting with a dichloromethane:methanol (98:2) mixture.
Yield=100%.

30.2. 6-Methyl-2-oxo-3-[[(phenylmethoxy)-carbonyl]amino]-4-(phenylthio)-1,2-dihydropyridine-1-acetic Acid 2.45 g (5.6 mmol) of methyl 6-methyl-2-oxo-3-[[(phenylmethoxy)carbonyl]amino]-4-(phenylthio)-1,2-dihydropyridine-1-acetate are hydrolysed under the conditions described in Example 3.
1.8 g of product are obtained which are recrystallized from ethanol.
Yield=76%; Melting point=176–178° C.

EXAMPLE 31 (compound No. 7)

Methyl 6-methyl-3-nitro-2-oxo-4-(phenylsulphonyl)-1,2-dihydropyridine-1-acetate 5.24 g (14 mmol) of methyl 6-methyl-3-nitro-2-oxo-4-[[(trifluoromethyl)sulphonyl]oxy]-1,2-dihydropyridine-1-acetate in solution in 50 ml of tetrahydrofuran are added dropwise to 2.38 g (14.5 mmol) of sodium benzenesulphinate in suspension in 100 ml of tetrahydrofuran and the mixture is left for 3 hours at room temperature. The solvent is evaporated off, the residue is taken up in 200 ml of dichloromethane and washed with 50 ml of a 1 N aqueous hydrochloric acid solution. The organic phase is recovered, it is dried over magnesium sulphate and evaporated off.
4.7 g of product are obtained which are recrystallized from an ethanol:water mixture.
Yield=92%; Melting point=142–143° C.

EXAMPLE 32 (compound No. 25)

3-Amino-6-methyl-2-oxo-4-(phenylsulphonyl)-1,2-dihydropyridine-1-acetic Acid 32.1. Methyl 3-amino-6-methyl-2-oxo-4-(phenylsulphonyl)-1,2-dihydropyridine-1-acetate 2.18 g (5.95 mmol) of methyl 6-methyl-3-nitro-2-oxo-4-(phenylsulphonyl)-1,2-dihydropyridine- 1-acetate are hydrogenated under the conditions described in Example 2.
2 g of product are obtained in the form of a white solid which is used as such in the next stage.

32.2. 3-Amino-6-methyl-2-oxo-4-(phenylsulphonyl)-1,2-dihydropyridine-1-acetic Acid 5.7 ml of a 1 N aqueous sodium hydroxide solution and 5.7 ml of ethanol are added to 1.6 g (4.76 mmol) of methyl 3-amino-6-methyl-2-oxo-4-(phenylsulphonyl)-1,2-dihydropyridine-1-acetate. 1.5 ml of dichloromethane are then introduced and the mixture is kept stirred for 2 hours at room temperature. The reaction medium is concentrated under vacuum and 8 ml of water and 5.8 ml of a 1 N aqueous hydrochloric acid solution are added. The precipitate is filtered, it is rinsed with water and it is dried under vacuum.
1.39 g of product are obtained in the form of a pale yellow powder.
Yield=91%; Melting point=203° C.

EXAMPLE 33 (compound No. 31)

3-[(Methoxycarbonyl)amino]-6-methyl-2-oxo-4-(phenylsulphonyl)-1,2-dihydropyridine-1-acetic Acid 0.95 g (2.62 mmol) of methyl 3-[(methoxycarbonyl)amino]-6-methyl-2-oxo-4-(phenylthio)-1,2- dihydropyridine-1-acetate is dissolved in 20 ml of dichloromethane, 0.925 g (5.36 mmol) of 3-chloroperoxybenzoic acid is added at 0° C. and the mixture is left overnight at room temperature. The reaction medium is cooled, evaporated and the residue taken up in 20 ml of ethyl acetate. The medium is washed successively with 20 ml of a half-saturated sodium bicarbonate solution, 20 ml of water and 20 ml of a saturated sodium chloride solution. It is dried over magnesium sulphate and evaporated. 1.06 g of product are obtained.

Yield=100%.

1.06 g (2.69 mmol) of ester are saponified according to the method described in Example 3.

0.77 g of product is obtained in the form of white crystals.

Yield=75%; Melting point=188° C.

TABLE

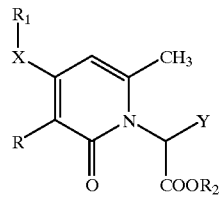

(I)

| No. | R | $R_1$ | $R_2$ | X | Y | Melting point (° C.) |
|---|---|---|---|---|---|---|
| 1 | —$NO_2$ | —$CH(CH_3)_2$ | —$CH_3$ | —O— | —H | 158 |
| 2 | —$NO_2$ | —$CH(CH_3)_2$ | —$CH_3$ | —$CH_2$— | —H | 128 |
| 3 | —$NO_2$ | cyclohexyl-$CH_2$ | —$CH_3$ | —$CH_2$— | —H | 128 |
| 4 | —$NO_2$ | phenyl-$CH_2$ | —$CH_3$ | —O— | —H | 239 |
| 5 | —$NO_2$ | phenyl-$CH_2$ | —$CH_3$ | —S— | —H | 195 |
| 6 | —$NO_2$ | phenyl-$CH_2$ | —$CH_3$ | —$CH_2$— | —H | 146–147 |
| 7 | —$NO_2$ | phenyl-$CH_2$ | —$CH_3$ | —$SO_2$— | —H | 142–143 |
| 8 | —$NO_2$ | 4-fluorophenyl-$CH_2$ | —$CH_3$ | —$CH_2$— | —H | 150 |

TABLE-continued
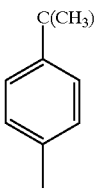
(I)
| No. | R | R₁ | R₂ | X | Y | Melting point (°C.) |
|---|---|---|---|---|---|---|
| 9 | —NO₂ | 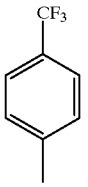 4-C(CH₃)₃-C₆H₄- | —CH₃ | —CH₂— | —H | 135 |
| 10 | —NO₂ | 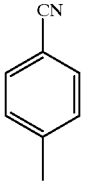 4-CF₃-C₆H₄- | —CH₃ | —CH₂— | —H | 155 |
| 11 | —NO₂ | 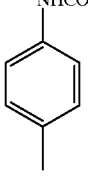 4-CN-C₆H₄- | —CH₃ | —CH₂— | —H | 195–196 |
| 12 | —NO₂ | 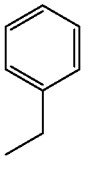 4-NHCOCH₃-C₆H₄- | —CH₃ | —CH₂— | —H | 215 |
| 13 | —NO₂ | 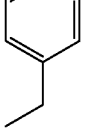 3-C₂H₅-C₆H₄- | —CH₃ | —S— | —H | 200 |
| 14 | —NO₂ | 3-C₂H₅-C₆H₄- | —CH₃ | —CH₂— | —H | 120–121 |

TABLE-continued
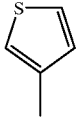
(I)
| No. | R | R₁ | R₂ | X | Y | Melting point (° C.) |
|---|---|---|---|---|---|---|
| 15 | —NO₂ | 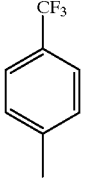 (3-thienyl) | —CH₃ | —CH₂— | —H | 157–158 |
| 16 | —NO₂ |  (4-CF₃-phenyl) | —H | —CH₂— | —H | 224 |
| 17 | —NH₂ | —CH(CH₃)₂ | —CH₃ | —CH₂— | —H | 122 |
| 18 | —NH₂ |  (phenyl) | —CH₃ | —O— | —H | 105–106 |
| 19 | —NH₂ |  (phenyl) | —CH₃ | —S— | —H | 65–66 |
| 20 | —NH₂ | 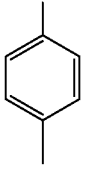 (phenyl) | —CH₃ | —CH₂— | —H | 135 |
| 21 | —NH₂ | 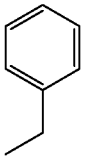 (4-F-phenyl) | —CH₃ | —CH₂— | —H | 151 |
| 22 | —NH₂ | (3-ethylphenyl) | —CH₃ | —S— | —H | 175 |

TABLE-continued
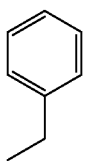
(I)
| No. | R | R₁ | R₂ | X | Y | Melting point (°C.) |
|---|---|---|---|---|---|---|
| 23 | —NH₂ | 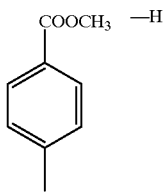 | —CH₃ | —CH₂— | —H | 96–97 |
| 24 | —NH₂ |  | —H | —CH₂— | —H | 178–180 |
| 25 | —NH₂ |  | —H | —SO₂— | —H | 203 |
| 26 | —NHCOCH₃ | 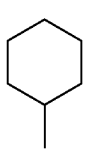 | —H | —CH₂ | —H | 200 |
| 27 | —NHCOCH₃ | 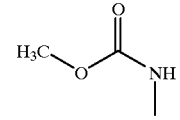 | —H | —O— | —H | 186(d) |
| 28 | 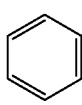 | —CH(CH₃)₂ | —H | —CH₂— | —H | 154 |
| 29 | 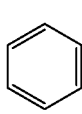 |  | —H | —O— | —H | 170 |
| 30 |  |  | —H | —CH₂— | —H | 170 |

TABLE-continued
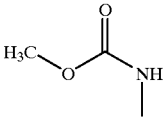
(I)
| No. | R | R₁ | R₂ | X | Y | Melting point (° C.) |
|---|---|---|---|---|---|---|
| 31 |  | 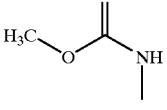 | —H | —SO₂— | —H | 188 |
| 32 | 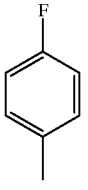 | 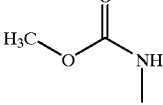 | —H | —CH₂— | —H | 166 |
| 33 | 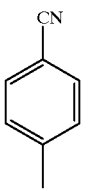 | 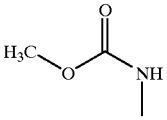 | —H | —CH₂— | —H | 125–130 |
| 34 | 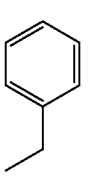 | 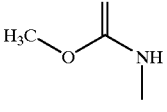 | —H | —S— | —H | 200 |
| 35 | 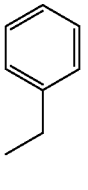 | 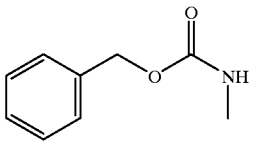 | —H | —CH₂— | —H | 132–134 |
| 36 | 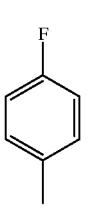 | 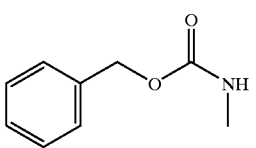 | —CH₃ | —CH₂— | —H | 236 |
| 37 | 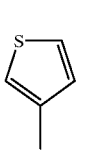 | | —CH₃ | —CH₂— | —H | 127–128 |

TABLE-continued
(I)
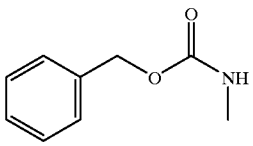
| No. | R | R₁ | R₂ | X | Y | Melting point (° C.) |
|---|---|---|---|---|---|---|
| 38 | 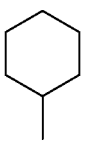 | 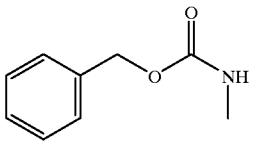 | —H | —CH₂— | —H | 150 |
| 39 | 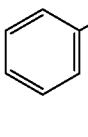 | 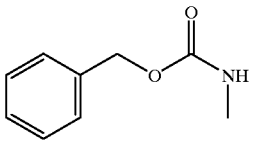 | —H | —O— | —H | 108–110 |
| 40 | 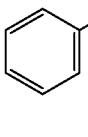 | 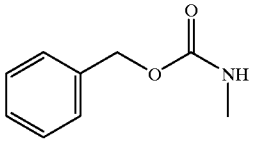 | —H | —S— | —H | 176–178 |
| 41 | 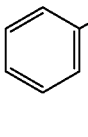 | 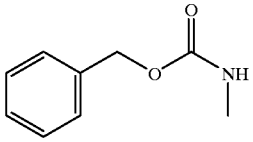 | —H | —CH₂— | —H | 158–160 |
| 42 | 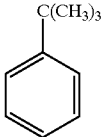 | 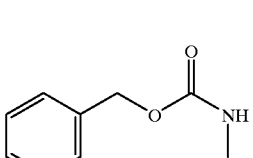 | —H | —CH₂— | —H | 200 |
| 43 |  | 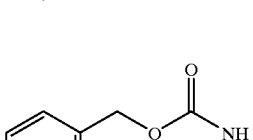 | —H | —CH₂— | —H | 171–172 |
| 44 | 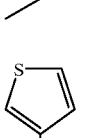 | | —H | —CH₂— | —H | 153–155 |

TABLE-continued (I)

Structure: pyridone core with substituents R, R₁ at position with X-R₁, CH₃, and N-CH(Y)-COOR₂

| No. | R | R₁ | R₂ | X | Y | Melting point (° C.) |
|---|---|---|---|---|---|---|
| 45 | H₃C-NH-C(O)-NH- (butyl urea) | | phenyl | —H | —CH₂— | —H | 197 |
| 46 | Ph-NH-C(O)-NH- | phenyl | —H | —CH₂— | —H | 168 |
| 47 | PhCH₂-NH-C(O)-NH- | phenyl | —H | —CH₂— | —H | 176 |
| 48 | H₃C-SO₂-NH- | phenyl | —H | —CH₂— | —H | 180 |
| 49 | H₃C-CH₂-SO₂-NH- | phenyl | —H | —CH₂— | —H | 205 |
| 50 | Ph-SO₂-NH- | phenyl | —H | —CH₂— | —H | 160–165 |
| 51 | PhCH₂-SO₂-NH- | phenyl | —H | —CH₂— | —H | >200 |
| 52 | morpholino-SO₂-NH- | phenyl | —H | —CH₂— | —H | 158(d) |
| 53 | 2-pyridyl-CH₂-NH- | phenyl | —H | —CH₂— | —H | 63(d) |

Notes:
In the "Melting point" column (d) corresponds to melting with decomposition The compounds of formula (I) according to the invention are useful as synthesis intermediates. They may be useful for preparing for example compounds of formula (1) described in Patent Application FR 9700379

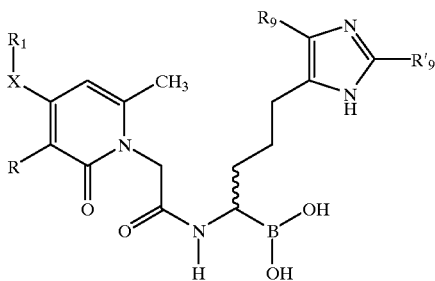

(1)

in which R, $R_1$ and X are as defined above and $R_9$ and $R'_9$ each represent, independently of each other, a hydrogen atom or a ($C_1$–$C_4$)alkyl group.

The synthesis of the compounds of formula (1) from the compounds of formula (I) according to the invention is illustrated in scheme 4.

A compound of formula (I) in which R, $R_1$ and X are as defined above and $R_2$ represents a hydrogen atom is reacted with N-hydroxysuccinimide in the presence of a coupling agent such as, for example, 1,3-dicyclohexyl-carbodiimide so as to prepare a compound of formula (VII) which is condensed with a compound of formula (VIII) in which $R_{10}$ and $R_{11}$ together represent the residue of a dihydroxylated compound such as for example butane-2,3-diol, 2,3-dimethylbutane-2,3-diol or (1α, 3α, 5α)-2,6,6-trimethylbicyclo[3.1.1]heptane-2,3-diol [(+)-α-pinanediol], in the presence of a base such as for example triethylamine and an intermediate compound is obtained which is treated with phenylboronic acid.

Example A which follows illustrates, without limiting it, the use of the compounds of formula (I) as synthesis intermediates. such as for example triethylamine and an intermediate compound is obtained which is treated with phenylboronic acid.

Example A which follows illustrates, without limiting it, the use of the compounds of formula (I) as synthesis intermediates.

Scheme 4

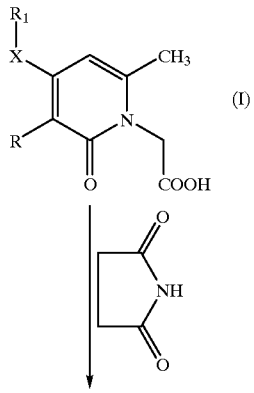

(I)

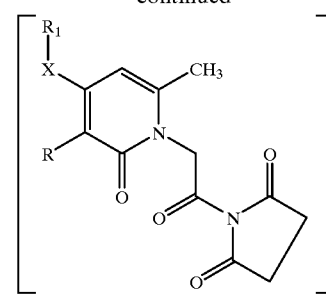

(VII)

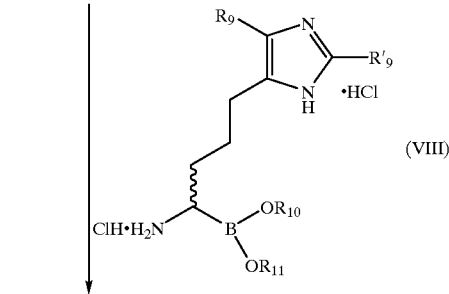

(VIII)

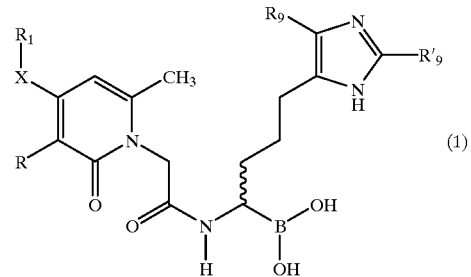

(1)

EXAMPLE A (R)-N-[borono[3-(1H-imidazol-4-yl)propyl]methyl]-3-[(phenylmethoxycarbonyl)amino]-6-methyl-2-oxo-4-phenoxy-1,2-dihydropyridine-1-acetamide Hydrochloride (1:1)

1 g (2.45 mmol) of 6-methyl-2-oxo-4-phenoxy-3-[[(phenylmethoxy)carbonyl]amino]-1,2-dihydropyridine-1-acetic acid is dried by azeotropic distillation with three times 20 ml of toluene and then it is dissolved in 70 ml of ethyl acetate and 45 ml of dichloromethane. 300 mg (2.6 mmol) of N-hydroxysuccinimide and 530 mg (2.6 mmol) of 1,3-dicyclohexylcarbodiimide are added successively and the reaction medium is kept stirred overnight at room temperature. The medium is filtered, the residue is taken up in 50 ml of ethyl acetate and again filtered. It is evaporated, the residue is taken up in 75 ml of dichloromethane and 1.5 g (3.85 mmol) of [3aS-2(R),3aα, 4β, 6 β, 7aα]]α-[3a,5,5-trimethylhexahydro-4,6-methano-1,3,2-benzodioxaborol-2-yl)-1H-imidazole-4-butanamine in solution in 75 ml of dichloromethane and 1.2 ml (8.61 mmol) of triethylamine are added. The reaction medium is kept stirred overnight at room temperature. The solvent is evaporated off and the residue is taken up in 50 ml of ethyl acetate and the organic phase is recovered. The medium is washed successively with a saturated sodium hydrogen carbonate solution, a saturated sodium chloride solution, dried over sodium sulphate and evaporated. The residue is taken up in 50 ml of a 0.1 N hydrochloric acid solution in isopropanol and evaporated. 1.5 g of product are obtained in the form of a foam which is taken up in 100 ml of a water:ether (1:1) mixture and 1.5 g (12.3 mmol) of phenylboronic acid and the mixture is kept stirred for 2 hours. The aqueous phase is recovered, it is washed five times with 50 ml of ether and evaporated. The residue is purified by chromatography on an RP 18 column, eluting with a 0.01 N hydrochloric acid:acetonitrile (8:2) mixture. The fractions are combined and evaporated, the product is taken up in water and lyophilised.

350 mg of product are obtained in the form of a white powder.

Yield=23%; Melting point=165° C.; $[\alpha]_d^{20}$=−2.5° (c=0.2; water).

What is claimed is:

1. A compound of formula (I)

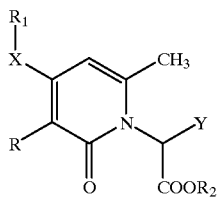

(I)

in which

R is an —$NO_2$ group or an —$NHR_3$ group, $R_3$ being a hydrogen atom, a —$COR_4$ group (where $R_4$ is selected from the ($C_1$–$C_4$)alkyl, aryl and aryl($C_1$–$C_4$)alkyl groups), a —$COOR_5$, group (where $R_5$ is selected from the ($C_1$–$C_4$)alkyl and aryl($C_1$–$C_4$)alkyl groups), a —$CONHR_6$ group, an —$SO_2R_6$, group (where $R_6$ is selected from the ($C_1$–$C_5$)alkyl, aryl and aryl($C_1$–$C_4$)alkyl groups), or an —$SO_2NR_7R_8$ group (where $R_7$ and $R_8$ are each, independently of each other, a hydrogen atom or a ($C_1$–$C_4$)alkyl group or form with the nitrogen atom carrying them a morpholine group), an aryl($C_1$–$C_4$) alkyl group (the aryl group being unsubstituted or substituted with a halogen atom, a linear or branched ($C_1$–$C_5$)alkyl group, a trifluoromethyl group, a cyano group, a ($C_1$–$C_4$)alkoxycarbonyl group or a ($C_1$–$C_4$) acylamino group), or a pyridyl($C_1$–$C_4$)alkyl group, or a thienyl($C_1$–$C_4$)alkyl group;

$R_1$ is a linear or branched ($C_1$–$C_4$)alkyl group, a cyclo($C_3$–$C_8$)alkyl group, an aryl group (the aryl group being unsubstituted or substituted with a halogen atom, a linear or branched ($C_1$–$C_5$)alkyl group, a trifluoromethyl group, a cyano group, a ($C_1$–$C_4$)alkoxycarbonyl group or a ($C_1$–$C_4$)acylamino group), an aryl($C_1$–$C_4$) alkyl group (the aryl component of the aryl($C_1$–$C_4$) alkyl group being unsubstituted or substituted with a halogen atom, a linear or branched ($C_1$–$C_5$)alkyl group, a trifluoromethyl group, a cyano group, a ($C_1$–$C_4$) alkoxycarbonyl group or a ($C_1$–$C_4$)acylamino group), or a pyridyl or thienyl group;

$R_2$ is a hydrogen atom, a ($C_1$–$C_4$)alkyl group, or an arylmethyl group;

X is an oxygen or sulphur atom, or a —$CH_2$—, —$SO_2$ or —$NR_1$— group where $R_1$ is as defined above; and Y is a hydrogen atom or a linear or branched ($C_1$–$C_6$)alkyl group.

2. A compound as claimed in claim 1, in which Y is a hydrogen atom.

3. A compound as claimed in claim 2, in which $R_1$ is a linear or branched ($C_1$–$C_4$)alkyl group or a cyclo($C_3$–$C_8$)alkyl group;

X is an oxygen atom; and $R_2$ a hydrogen atom or a ($C_1$–$C_4$)alkyl group.

4. A compound as claimed in claim 2, in which $R_1$ is an aryl group (unsubstituted or substituted with a halogen atom, a linear or branched ($C_1$–$C_5$)alkyl group, a trifluoromethyl group, a cyano group or a ($C_1$–$C_4$)acylamino group), an aryl($C_1$–$C_4$)alkyl group (the aryl component being unsubstituted or substituted with a halogen atom, a linear or branched ($C_1$–$C_5$)alkyl group, a trifluoromethyl group, a cyano group or a ($C_1$–$C_4$)acylamino group), or a pyridyl or thienyl group;

X is a sulphur atom or a —$CH_2$—, —$SO_2$— or —$NR_1$— group; and $R_2$ a hydrogen atom or a ($C_1$–$C_4$)alkyl group.

5. A compound as claimed in claim 2, in which $R_1$ is a linear or branched ($C_1$–$C_4$)alkyl group or a cyclo($C_3$–$C_8$)alkyl group;

X is a sulphur atom or an —$NR_1$— group; and $R_2$ a hydrogen atom or a ($C_1$–$C_4$)alkyl group.

6. A compound as claimed in claim 2, in which $R_1$ is a pyridyl or thienyl group or an aryl group (unsubstituted or substituted with a halogen atom, a linear or branched ($C_1$–$C_5$)alkyl group, a trifluoromethyl group, a cyano group or a ($C_1$–$C_4$)acylamino group);

X is an oxygen atom; and $R_2$ a hydrogen atom or a ($C_1$–$C_4$)alkyl group.

7. A compound as claimed in claim 2, in which $R_1$ is an aryl group (unsubstituted or substituted with a halogen atom, a linear or branched ($C_1$–$C_5$)alkyl group, a trifluoromethyl group, a cyano group or a ($C_1$–$C_4$) acylamino group) or an aryl($C_1$–$C_4$)alkyl group (the aryl component being unsubstituted or substituted with a halogen atom, a linear or branched ($C_1$–$C_5$)alkyl group, a trifluoromethyl group, a cyano group or a ($C_1$–$C_4$)acylamino group), or a pyridyl or thienyl group;

R is an —$NO_2$ or —$NH_2$ group; and $R_2$ is a hydrogen atom or an arylmethyl group.

8. A compound as claimed in claim 2, in which $R_1$ is an aryl or aryl($C_1$–$C_4$)alkyl group which are substituted with a ($C_1$–$C_4$)alkoxycarbonyl group;

X is an oxygen atom; and

R is an —$NO_2$ or —$NH_2$ group; and $R_2$ is a hydrogen atom or an arylmethyl group.

9. A process for preparing a compound of claim 2, in which $R_1$ is either a linear or branched ($C_1$–$C_4$)alkyl group or a cyclo($C_3$–$C_5$)alkyl group; X is an oxygen atom; $R_2$ is a hydrogen atom or a ($C_1$–$C_4$)alkyl group;

$R_3$ is a hydrogen atom, a —$COR_4$ group (where $R_4$ is selected from the ($C_1$–$C_4$)alkyl, aryl and aryl($C_1$–$C_4$) alkyl groups), a —$COOR_5$, group (where $R_5$ is selected from the ($C_1$–$C_4$)alkyl and aryl($C_1$–$C_4$)alkyl group), a —$CONHR_6$ group, an —$SO_2R_6$, group (where $R_6$ is selected from the ($C_1$–$C_5$)alkyl, aryl and aryl($C_1$–$C_4$) alkyl groups), or an —$SO_2NR_7R_8$ group (where $R_7$ and $R_8$ are each, independently of each other, a hydrogen atom or a ($C_1$–$C_4$)alkyl group or form with the nitrogen atom carrying them a morpholine group), an aryl ($C_1$–$C_4$)alkyl group (the aryl group being unsubstituted or substituted with a halogen atom, a linear or branched ($C_1$–$C_5$)alkyl group, a trifluoromethyl group, a cyano group, a ($C_1$–$C_4$)alkoxycarbonyl group or a ($C_1$–$C_4$)

acylamino group), or a pyridyl($C_1$–$C_4$)alkyl group, or a thienyl($C_1$–$C_4$)alkyl group and;

Y is a hydrogen atom or a linear or branched($C_1$–$C_6$)alkyl group, which comprises reacting a compound of formula (II), (II)

in which Y is as defined as above and Alk is a ($C_1$–$C_4$)alkyl group, with a compound of formula $R_1$OH to produce a compound of formula (Ia)

(Ia)

in which $R_1$, Y, and Alk are as defined above.

10. A process as claimed in claim 9, which further comprises hydrogenating the compound of formula (Ia) to obtain a compound of formula (Ib)

(Ib)

in which $R_1$, Y, and Alk are as defined in claim 9.

11. A process for preparing a compound of claim 2, which comprises treating a compound of formula (Ib)

(Ib)

in which Alk is a ($C_1$–$C_4$)alkyl group and $R_1$ and Y are as defined in claim 2, with a compound $R_3$-Hal, where Hal is a halogen atom and $R_3$ is as defined in claim 2 but is other than hydrogen; or subjecting the compound of formula (Ib) to a reductive amination when $R_3$ is an aryl($C_1$–$C_4$)alkyl group to obtain a compound of formula (Ic)

(Ic)

in which $R_1$, $R_3$, Y, and Alk are as defined above.

12. A process as claimed in claim 11, which further comprises saponificating the compound of formula (1c) with sodium or lithium hydroxide to obtain a compound of formula (Id)

(Id)

in which $R_1$, $R_3$, and Y are as defined in claim 16.

13. A process for preparing a compound of claim 2, in which $R_1$ is an aryl group (unsubstituted or substituted with a halogen atom, a linear or branched ($C_1$–$C_5$)alkyl group, a trifluoromethyl group, a cyano group or a ($C_1$–$C_4$) acylamino group), a pyridyl or thienyl group or an aryl($C_1$–$C_4$)alkyl group (the aryl component being unsubstituted or substituted with a halogen atom, a linear or branched ($C_1$–$C_5$)alkyl group, a trifluoromethyl group, a cyano group or a ($C_1$–$C_4$)acylamino group), X is a sulphur atom or a —$CH_2$—, —$SO_2$— or —$NR_1$— group, $R_2$ is a hydrogen atom or a ($C_1$–$C_4$)alkyl group, and $R_3$ and Y are as defined in claim 2; or $R_1$ is a linear or branched ($C_1$–$C_4$)alkyl group or a cyclo ($C_3$–$C_8$)alkyl group, X is a sulphur atom or an —$NR_1$— group, $R_2$ is a hydrogen atom or a ($C_1$–$C_4$)alkyl group, and $R_3$ and Y are as defined in claim 2; or $R_1$ is a pyridyl or thienyl group or an aryl group (unsubstituted or substituted with a halogen atom, a linear or branched ($C_1$–$C_5$)alkyl group, a trifluoromethyl group, a cyano group or a ($C_1$–$C_4$)acylamino group), X is an oxygen atom, $R_2$ is a hydrogen atom or a ($C_1$–$C_4$)alkyl group, and $R_3$ and Y are as defined in claim 2, which comprises converting the alcohol function of the compound of formula (II)

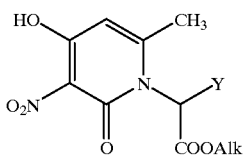

(II)

where Y is as defined in claim 2 and Alk is a $(C_1-C_4)$alkyl group, to obtain a compound of formula (III)

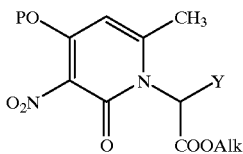

(III)

in which

OP is a leaving group; and reacting the compound of formula (III) either with a compound of formula $R_1XH$, where X is other than $—CH_2—$, or with an organometallic $R_1CH_2Cu(CN)ZnHal$ compound, where Hal is a halogen atom and X is $—CH_2—$, to obtain a compound of formula (Ie)

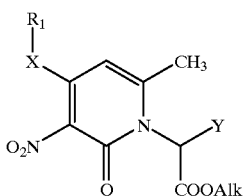

(Ie)

in which $R_1$, X, Y, and Alk are as defined above.

14. A process as claimed in claim 13, which further comprises hydrogenating the compound of formula (Ie) when X is an oxygen atom, a $—CH_2—$, $—SO_2—$ or $—NR_1—$ group, or treating the compound of formula (Ie) with zinc in acidic medium when X is a sulphur atom to obtain a compound of formula (If)

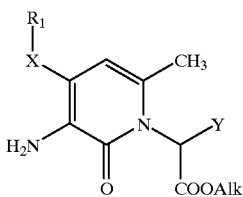

(If)

in which $R_1$, X, Y and Alk are as defined in claim 13.

15. A process as claimed in claim 14, which further comprises treating the compound of formula (If) either with a compound $R_3$-Hal, where Hal is a halogen atom and $R_3$ is other than hydrogen, or with a compound of formula $R_6NCO$, where $R_6$ is selected from $(C_1-C_5)$alkyl, aryl, and aryl$(C_1-C_4)$alkyl groups; or subjecting the compound of formula (If) to a reductive amination when $R_3$ is an aryl $(C_1-C_4)$alkyl group to obtain a compound of formula (Ig)

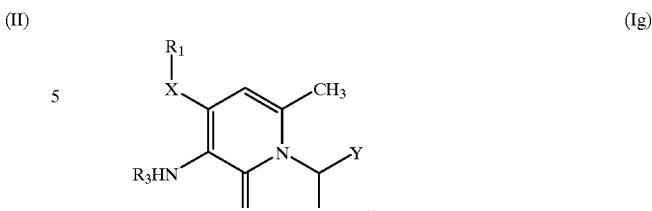

(Ig)

in which $R_1$, X, Y, and Alk are as defined in claim 14 and $R_3$ is as defined above.

16. A process as claimed in claim 15, which further comprises saponifying the compound of formula (Ig) with sodium or lithium hydroxide to obtain a compound of formula (Ih)

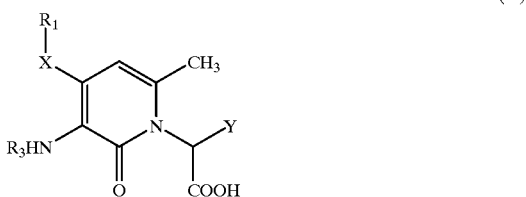

(Ih)

in which $R_1$, X, Y, and $R_3$ are as defined in claim 15.

17. A process as claimed in claim 13, which further comprises, when X is $—CH_2—$, saponifying the compound of formula (Ie) with sodium or lithium hydroxide to obtain a compound of formula (Ii)

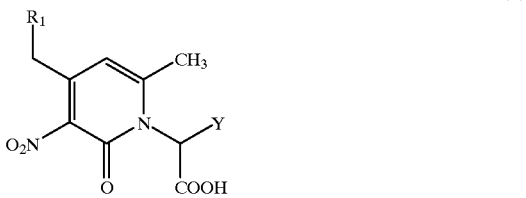

(Ii)

in which $R_1$ and Y are defined as in claim 13.

18. A process for preparing a compound of claim 2, in which $R_1$ is an aryl or aryl$(C_1-C_4)$alkyl group, the aryl group or aryl component of the aryl$(C_1-C_4)$alkyl group being substituted with a $(C_1-C_4)$alkoxycarbonyl group, which comprises:

(A) reacting a compound of formula (IV)

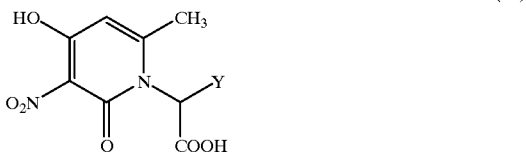

(IV)

in which Y is as defined in claim 2, with a compound of formula ArOH, where Ar represents an arylmethyl group, in the presence of 1,3-dicyclohexylcarbodiimide to obtain a compound of formula (V);

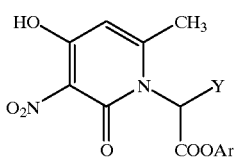

(V)

(B) protecting the alcohol function of the compound of formula (V) to obtain a compound of formula (VI)

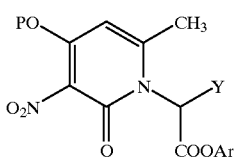

(VI)

in which OP is a leaving group; and (C) reacting the compound of formula (VI) with a compound of formula $R_1LXH$, where X is as defined in claim 2 but is other than —$CH_2$—, or with a compound of formula $R_1CH_2Cu(CN)ZnHal$, wherein Hal is a halogen atom and X is —$CH_2$—, to obtain a compound of formula (Ij)

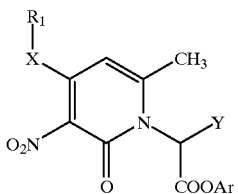

(Ij)

in which $R_1$ and Ar are as defined above, and X and Y are as defined in claim 2.

19. A process as claimed in claim 18, which further comprises subjecting the compound of formula (Ij) to a catalytic hydrogenation to obtain a compound of formula (Ik)

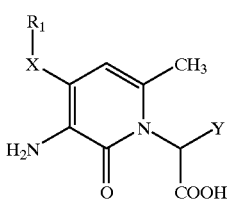

(Ik)

in which $R_1$, X and Y are as defined in claim 18.

20. A process for preparing compounds of formula (1)

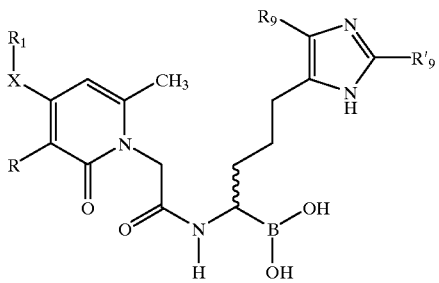

(1)

in which R, $R_1$ and X are as defined in claim 2, and $R_9$ and $R'_9$ each are, independently of each other, a hydrogen atom or a ($C_1$–$C_4$)alkyl group, which comprises:

(A) reacting a compound of formula (I) according to claim 2, in which $R_2$ and Y are hydrogen atoms, with N-hydroxysuccinimide in the presence of a coupling agent to obtain a compound of formula (VII)

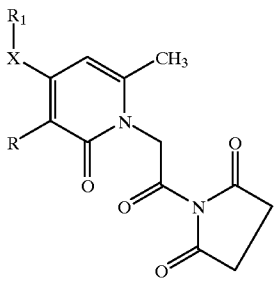

(VII)

(B) condensing the compound of formula (VII) with a compound of formula (VIII)

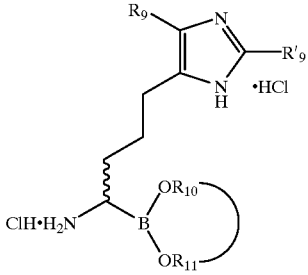

(VIII)

in which $R_{10}$ and $R_{11}$ together are the residue of a dihydroxylated compound in the presence of a base; and (C) treating the product of the condensing step with phenylboronic acid to obtain a compound of formula (1).

21. A process as claimed in claim 20, in which the dihydroxylated compound in the condensing step is butane-2,3-diol, 2,3-dimethylbutane-2,3-diol, or (1α,3 α,5α)-2,6,6-trimethylbicycloheptane-2,3-diol.

22. A mixture of pure enantiomers of the compound as claimed in claim 1, or mixture of different enantiomers of the compound.

23. A mixture as claimed in claim 22, wherein the mixture is a racemic mixture of the different enantiomers of the compound.

* * * * *

UNITED STATES PATENT AND TRADEMARK OFFICE
CERTIFICATE OF CORRECTION

PATENT NO. : 6,252,082 B1
DATED : June 26, 2001
INVENTOR(S) : Lassalle et al.

It is certified that error appears in the above-identified patent and that said Letters Patent is hereby corrected as shown below:

<u>Title page,</u>
Item [57] ABSTRACT,
Line 15, "-SO$_2$" should read -- SO$_2$- --.

<u>Column 35, claim 1,</u>
Line 29, "-COOR$_5$, group" should read -- COOR$_5$ group --.
Lines 31-32, "-SO$_2$R$_6$, group" should read -- SO$_2$R$_6$ group --.

<u>Column 36, claim 4,</u>
Line 5, "(C$_1$-C$_5$,)alkyl" should read -- (C$_1$-C$_5$)alkyl --.

<u>Column 36, claim 9,</u>
Line 52, "cyclo(C$_3$-C$_5$)alkyl" should read -- cyclo(C$_3$-C$_8$)alkyl --.
Line 56, "-COOR$_5$, group" should read -- COOR$_5$ group --.
Line 57, "group" should read -- groups --.
Line 58, "-SO$_2$R$_6$, group" should read -- SO$_2$R$_6$ group --.

<u>Column 38, claim 12,</u>
Line 16, "formula (1c)" should read -- formula (Ic) --.
Line 32, "claim 16" should read -- claim 11 --.

<u>Column 41, claim 18,</u>
Line 27, "R$_1$LXH" should read -- R$_1$XH --.

<u>Column 42, claim 21,</u>
Line 57, "trimethylbicycloheptane-2,3-diol" should read -- trimethylbicyclo[3.1.1] heptane-2,3-diol [(+) -α-pinanediol] --.

Signed and Sealed this

Fifth Day of March, 2002

Attest:

*Attesting Officer*

JAMES E. ROGAN
*Director of the United States Patent and Trademark Office*